US011033480B2

(12) United States Patent
McConaughy et al.

(10) Patent No.: US 11,033,480 B2
(45) Date of Patent: Jun. 15, 2021

(54) SKIN CARE COMPOSITION

(71) Applicant: The Procter & Gamble Company, Cincinnati, OH (US)

(72) Inventors: Shawn David McConaughy, Cincinnati, OH (US); Jorge Max Sunkel, West Chester, OH (US); Rebecca Lynn Boland, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 430 days.

(21) Appl. No.: 15/475,519

(22) Filed: Mar. 31, 2017

(65) Prior Publication Data

US 2018/0280282 A1 Oct. 4, 2018

(51) Int. Cl.
*A61K 8/891* (2006.01)
*A61K 8/67* (2006.01)
*A61K 8/895* (2006.01)
*A61Q 19/00* (2006.01)
*A61K 8/89* (2006.01)

(52) U.S. Cl.
CPC .............. *A61K 8/891* (2013.01); *A61K 8/671* (2013.01); *A61K 8/89* (2013.01); *A61K 8/895* (2013.01); *A61Q 19/00* (2013.01); *A61Q 19/007* (2013.01); *A61K 2800/412* (2013.01); *A61K 2800/546* (2013.01); *A61K 2800/594* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 5,023,075 A | 6/1991 | Macchio et al. | |
| 7,915,214 B2 | 3/2011 | SenGupta et al. | |
| 9,415,002 B2 | 8/2016 | Lamberty et al. | |
| 2004/0223938 A1 | 11/2004 | Li et al. | |
| 2006/0078524 A1 | 4/2006 | Midha et al. | |
| 2006/0292100 A1* | 12/2006 | Nguyen | A61K 8/553 424/70.12 |
| 2007/0071780 A1 | 3/2007 | Dubois et al. | |
| 2008/0242573 A1 | 10/2008 | Wei | |
| 2011/0117225 A1 | 5/2011 | Wei et al. | |
| 2013/0039963 A1* | 2/2013 | Lorant | A61K 8/025 424/401 |
| 2013/0243835 A1* | 9/2013 | Tanner | A61K 8/8147 424/401 |
| 2017/0281478 A1 | 10/2017 | El-Khouri | |

FOREIGN PATENT DOCUMENTS

| | | | |
|---|---|---|---|
| WO | WO2005048959 A1 | | 6/2005 |
| WO | WO 2013/190710 | * | 12/2013 |
| WO | WO2013190710 A1 | | 12/2013 |

OTHER PUBLICATIONS https:// How to Convert from Centistoke to Centipoise by Chris Deziel; Updated Mar. 13, 2018, Sciencing 8279085.html [accessed Jul. 13, 2018 2:12:43 PM].*
Kambe, Hirotaro and Kazua Kamagata, A Method of Measuring Tackiness, Journal of Applied Polymer Science, vol. 13, pp. 493-504 (1969).*
International Search Report and Written Opinion of the International Searching Authority, PCT/US2018/023233, dated May 30, 2018, 21 pages.

* cited by examiner

Primary Examiner — David J Blanchard
Assistant Examiner — Sarah J Chickos
(74) Attorney, Agent, or Firm — John G. Powell

(57) ABSTRACT

A personal care composition for cosmetic treatment of skin that provides an improved moisturization signal to a user and exhibits good feel properties. The composition includes a dimethicone fluid or a blend of dimethicone fluids with a viscosity of greater than 1000 centistokes (cSt). The dimethicone fluid(s) are configured to provide the composition with a Time Weighted Force Area of between $5 \times 10^4$ and $12 \times 10^4$ and a Mean Break Time of between 0.30 and 0.75.

16 Claims, 5 Drawing Sheets

SKIN CARE COMPOSITION

FIELD OF THE INVENTION

The present invention generally relates to a topical skin care composition with improved consumer perceived moisturization and feel properties. More specifically, the present invention relates to a personal care composition comprising a non-volatile dimethicone and suitable tack properties.

BACKGROUND OF THE INVENTION

Many personal care products currently available to consumers are directed primarily to improving the health and/or appearance of skin. For example, there are a variety of topical skin care products available that are directed to delaying, minimizing, or even eliminating skin dryness, skin wrinkling, and other histological changes commonly associated with the aging of skin or environmental damage to human skin. As a result, the sale of personal care products has become a booming business in youth-conscious societies.

Perhaps equally as important to providing the desired benefit is the user's perception that the product is providing the benefit or a particular level of benefit. And in some instances a user may associate a benefit or a level of benefit with certain product aesthetics, which may or may not be the same as the product aesthetics that the consumer finds pleasing. For example, some consumers may desire a light, cool feeling when applying a skin moisturizer, but, counterintuitively, may associate a heavy, oily feeling with good moisturization.

Dimethicones, sometimes called polydimethylsiloxane or PDMS, have long been known for use in skin care compositions. Low viscosity dimethicone fluids (e.g., less than 5 centistokes) are commonly used in skin care compositions as carriers for delivering a wide range of ingredients to skin without leaving a heavy, greasy feel. However, these low viscosity dimethicone fluids may be perceived as dry due to their relatively high evaporation rates. Higher viscosity dimethicone fluids (e.g., greater than 10000 centistokes) are commonly used as carriers and skin conditioning agents. However, higher viscosity dimethicone fluids may be perceived as tacky or greasy feeling. Thus, there remains a need to find a suitable balance between perceived moisturization and the way the skin care product feels on skin.

PCT Publication WO 2013/190710 filed by Shimizu, et al., discloses dimethicones across a wide range of viscosities (e.g., less than 1500 cSt and greater than 5000 cSt) for use in cosmetic compositions for treating skin and lips. However, WO 2013/190710 fails to recognize the importance of selecting dimethicone(s) that provide suitable moisturization perception and product aesthetics.

Accordingly, it would be desirable to provide a personal care composition that provides a suitable balance between the perception of good moisturization and desirable product aesthetics.

SUMMARY OF THE INVENTION

Disclosed herein are personal care compositions that exhibits an improved moisturization signal and methods of using such compositions. In some instances, the composition comprises 5% to 30%, 10%-30%, or 10-20%, by weight of the composition, of a blend of at least two dimethicone fluids, wherein the blend of dimethicone fluids exhibits a viscosity of greater than about 1000 centistokes (cSt) according to the Rheology Method. The present compositions also include a dermatologically acceptable carrier and exhibit a Time Weighted Force Area of between $5\times10^4$ and $12\times10^4$ and a Mean Break Time of between 0.30 and 0.75 according to the Tack Method.

In some instances, the personal care compositions herein comprise a dimethicone fluid that has a viscosity of between 1000 cSt and 1,000,000 cSt according to the Rheology Method. In these instances, the compositions exhibit a Time Weighted Force Area of between $5\times10^4$ and $12\times10^4$ and a Mean Break Time of between about 0.30 and about 0.75 according to the Tack Method.

DETAILED DESCRIPTION OF THE INVENTION

Figure 1:
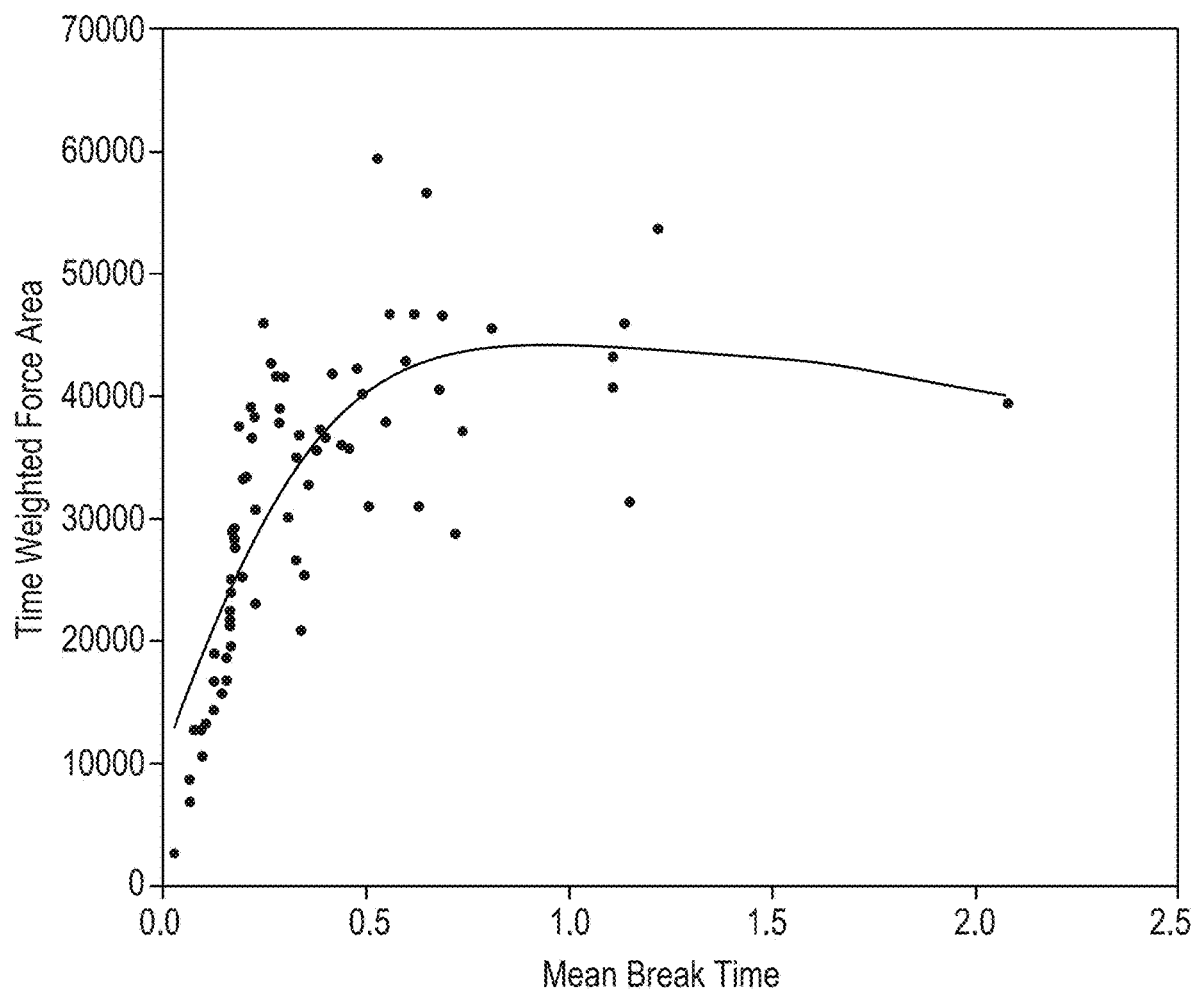
FIG. 1 is a plot of time weighted force average versus mean break time for a multitude of conventional skin care compositions.

At least some consumers desire a cosmetic skin care product that signals good moisturization while leaving the skin feeling smooth. For example, a user may associate the skin moisturizing properties of a skin care composition with a certain amount of tackiness on the skin after applying the composition. But if the tackiness persists for too long, then the undesirable feel properties of the composition may outweigh the perceived benefit to the user, resulting in discontinued use of the product. Surprisingly, it has been discovered that certain blends of dimethicone fluids can provide a suitable balance between good moisturization perception and desired product aesthetics.

As used in the description and the appended claims, the singular forms "a," "an," and "the" are intended to include the plural forms as well, unless the context clearly indicates otherwise. All percentages disclosed herein are by weight of the total composition, unless specifically stated otherwise. All ratios are weight ratios, unless specifically stated otherwise. The number of significant digits conveys neither a limitation on the indicated amounts nor on the accuracy of the measurements. All numerical amounts are understood to be modified by the word "about" unless otherwise specifically indicated.

All measurements herein are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified. All numeric ranges are inclusive of narrower ranges and combinable; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

Definitions

"About," as used herein, modifies a particular value, by referring to a range equal to the particular value, plus or minus twenty percent (+/−20%) or less (e.g., less than 15%, 10%, or even less than 5%).

"Active" means a compound that, when applied to keratinous tissue and/or a target portion of keratinous tissue, provides a benefit or improvement in the health, appearance, and/or feel of the keratinous tissue. The actives herein can be skin care actives, hair care actives, or a combination thereof.

"Apply" or "application", as used in reference to a composition, means to apply or spread the compositions of the present invention onto a human skin surface such as the epidermis.

"Derivative" means a molecule similar to that of another one, but differing from it with respect to a certain functional moiety (e.g., esters, ethers, amides, amines, carboxylic acids, hydroxyls, acetyls, thiols, halogens, thiols, and/or salt derivatives of the relevant molecule).

"Dermatologically acceptable" means that the compositions or components thereof so described are suitable for use in contact with mammalian keratinous tissue without undue toxicity, incompatibility, instability, allergic response, and the like.

"Disposed" means an element is positioned in a particular place relative to another element.

"Effective amount" means an amount of a compound or composition sufficient to significantly induce a positive benefit to keratinous tissue, such as a health, appearance, and/or feel benefit, including, independently or in combination, the benefits disclosed herein, but low enough to avoid serious side effects (i.e., to provide a reasonable benefit to risk ratio, within the scope of sound judgment of the skilled artisan). An effective amount of a retinoid is an amount of sufficient to regulate a desired condition of mammalian keratinous tissue when topically applied thereto in a personal care composition over the course of a treatment period.

"Keratinous tissue" refers to keratin-containing layers disposed as the outermost protective covering of mammals which includes, but is not limited to, skin, hair, nails, cuticles, etc.

"Personal care composition" means a topical composition for regulating a condition of mammalian keratinous tissue (e.g., skin, hair, finger nails). Some nonlimiting examples of personal care compositions include skin creams, lotions, and serums; shave prep compositions; body washes; deodorants and antiperspirants, shampoos; conditioners; combinations of these and the like.

"Regulating the condition of mammalian keratinous tissue," as used herein, means improving the health, appearance, and/or feel of keratinous tissue.

"Retinoid containing personal care products" refers to any personal care product that contains a retinoid. Preferred personal care products include products used for regulating the condition of skin, even more preferably reducing the appearance of skin aging and/or reducing the appearance or occurrence of skin acne. The retinoid containing personal care products herein may also exhibit an absence of significant (e.g., consumer-unacceptable) skin irritation and good aesthetics.

"Skin care composition" refers to topical personal care compositions for regulating and/or improving a skin condition. Some nonlimiting examples of skin care compositions include skin creams, moisturizers, lotions, and body washes.

"Stable," when referring to a retinoid contained in a personal care composition, means less than 25% (e.g., less than 20%, 15%, 10%, or even less than 5%) of the retinoid present in the personal care composition degrades (i.e., chemically converted to a different compound via, for example, oxidation or some other chemical process) when the composition is subjected to environmental conditions commonly experienced by a personal care compositions of the type (e.g., 40° C. for 2 or more weeks, 1 month or more, 2 months or more, or 3 months or more). In some instances, the retinoid may be stable at 50° C. for more than 2, 4, or even 8 weeks. A suitable method of determining retinoid stability is described in the HPLC Method in more detail below.

"Topical" refers to a composition that is intended to be applied to a bodily surface such as skin or hair.

"Viscosity" herein refers to kinematic viscosity reported in Stokes or centiStokes ("cSt"), unless specifically stated otherwise. Viscosity is determined according to the Rheology Method described in the Methods section below. When two or more non-volatile dimethicones are included in the present composition, "viscosity" refers to the viscosity of the resulting blend of non-volatile dimethicones.

Personal Care Composition

The cosmetic compositions herein are configured for topical application to keratinous tissue and include a non-volatile dimethicone fluid or a blend of non-volatile dimethicone fluids and, optionally, a silicone elastomer, a superabsorbent polymer, and/or a skin care active disposed in a dermatologically acceptable carrier. The individual ingredients are discussed in more detail below.

The dimethicone fluid or blend of dimethicone fluids in the preset compositions provides the desired tackiness. Tackiness, as used herein, is characterized by the relationship between the tack force and stringiness. It is believed, without being limited by theory, that the tack force and stringiness of a skin care composition are critical for providing the desired moisturization signal and aesthetic feel. Tack force generally refers to the peak force required to separate an object from the composition after contacting the composition. Stringiness generally refers to the time it takes for strands of the composition to break when an object in contact with the composition is moved away from the composition (i.e., how long a force must be applied to break contact). Suitable methods for determining tack force and stringiness are described in more detail below.

At least some users associate good moisturization with a high tack force, especially during and/or shortly after application of the product (e.g., less than 10, 9, 8, 7, 6, 5, 4, 3, 2, or even less than 1 minute after application). However, in conventional compositions, an increase in tack force is typically accompanied by an increase in stringiness. And while a user may tolerate or even desire some stringiness during and/or immediately after application as a signal of moisturization, it may be undesirable for the stringiness to persist, for example, more than 1, 2, 3, 4, 5, 6, 7, 8, 9, or even more than 10 minutes after application of the product. Accordingly, in some instances, the compositions herein exhibit a decrease in stringiness over time, as observed when the change in break time of the composition at initial application is higher than the break time at 60, 80, and/or 100 minutes according to the Tack Method. In some instances, it may be desirable for the composition to exhibit a decrease in break time of more than 0.5 (e.g., more than 0.6, 0.7, or even more than 0.8).

FIG. 1 is plot of Time Weighted Tack Force versus Mean Break Time for 76 commercially available skin care products. Each product is marketed for providing a skin moisturization benefit. As can be seen in FIG. 1, there is a trend in the products tested in which higher tack force generally correlates to higher stringiness. Thus, it would be desirable to provide a composition with a suitable tack force, but without the corresponding increase in stringiness The compositions herein have a Time Weighted Force Area of between $5 \times 10^4$ and $12 \times 10^4$ (e.g., between $6 \times 10^4$ and $11 \times 10^4$, $7 \times 10^4$ and $1 \times 10^5$, or even between $8 \times 10^4$ and $9 \times 10^4$) and a Mean Break Time of between 0.30 and 0.75 (e.g., between 0.35 and 0.7, 0.40 and 0.65, or even between 0.45 and 0.60). Additionally or alternatively, the present compositions may have a tack force at 60 minutes, 80 minutes, and/or 100 minutes of greater than 1000 g (e.g., greater than 1200 g, 1300 g, 1400 g, 1500 g, or even greater than 2000 g), according to the Tack Method.

Figure 2:
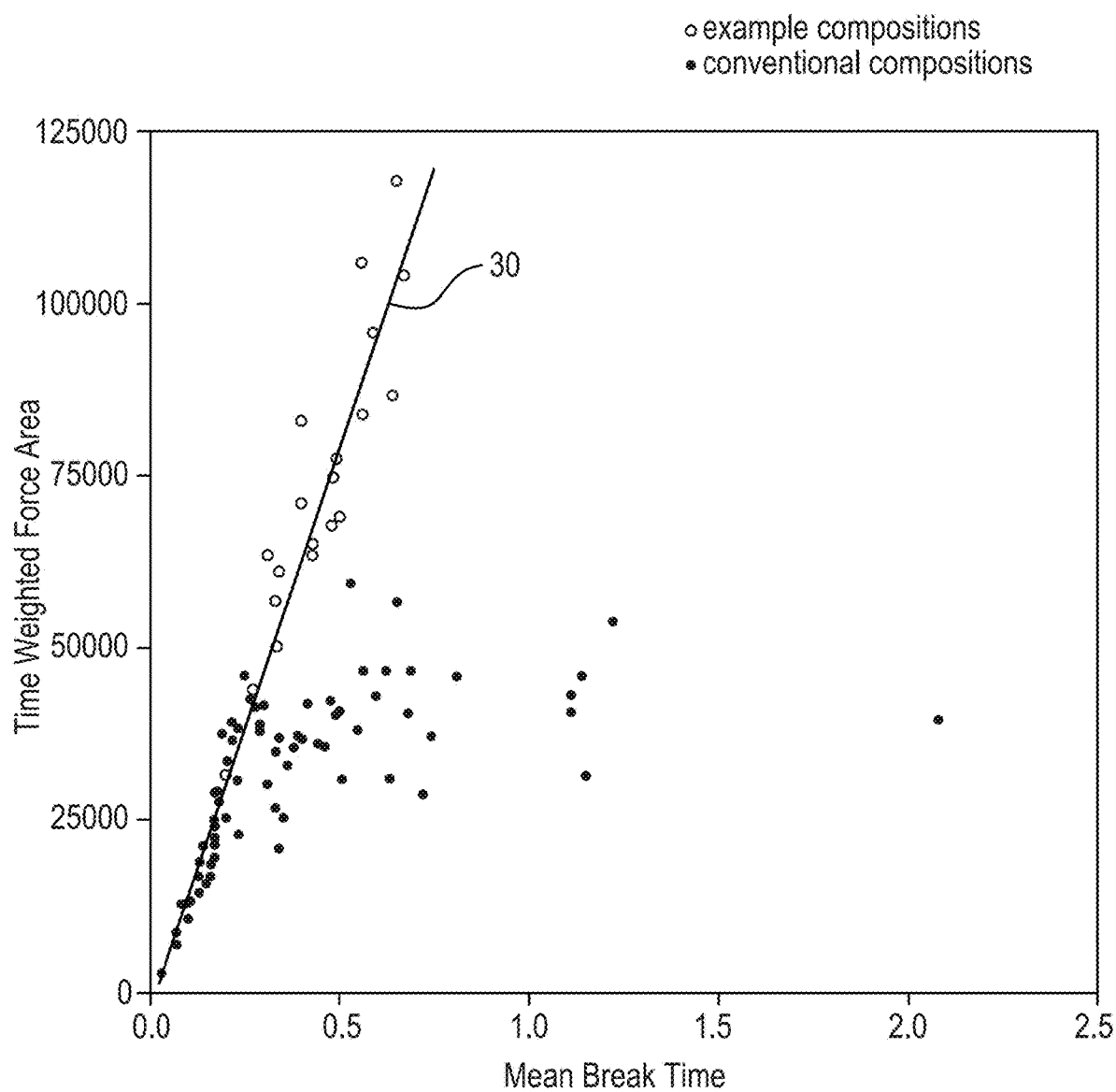
FIG. 2 is a plot of time weighted force average versus mean break time for examples of the present composition overlain on the plot of FIG. 1.

FIG. 2 is plot of the Time Weighted Tack Force versus Mean Break Time for the exemplary compositions of Tables 1A and 1B overlaid on the plot of FIG. 1. The plot includes a trend line 30 that indicates a suitable amount of tackiness according to the present disclosure. As can be seen in FIG. 2, the present compositions provide a relatively high tack force, but do not follow the trend of a corresponding higher stringiness as seen in conventional compositions.

Dermatologically Acceptable Carrier

The personal care compositions herein include a dermatologically acceptable carrier enables other components (e.g., actives) to be delivered to the skin at an appropriate concentration. The carrier can thus act as a diluent, dispersant, solvent, or the like for skin care actives and/or other optional ingredients, which helps ensure that the actives or other ingredients are applied to and distributed evenly over the selected target portion of skin at an appropriate concentration. The carrier may contain one or more dermatologically acceptable solid, semi-solid or liquid fillers, diluents, solvents, extenders and the like. The carrier can be inert or it can provide benefits of its own to keratinous tissue. Concentrations of the carrier can vary with the carrier selected and the intended concentrations of the composition components. As used herein, "diluent" includes materials in which the particulate material of the composition can be dispersed, dissolved, or otherwise incorporated. Nonlimiting examples of hydrophilic diluents are water, organic hydrophilic diluents such as lower monovalent alcohols (e.g., $C_1$-$C_4$) and low molecular weight glycols and polyols, including propylene glycol, polyethylene glycol (e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof. Suitable hydrophobic diluents include oils (e.g., silicones, hydrocarbons, esters, amides, ethers, and mixtures thereof). The oils used herein are typically fluid at room temperature and may be volatile or nonvolatile. Particularly suitable examples of hydrophobic diluents are silicone oils such as the nonvolatile dimethicone fluids described herein.

In some instances, the dermatologically acceptable carrier may be in the form of a stable emulsion made using conventional methods for making emulsions. The emulsion may be an oil-in-water or water-in-oil emulsion, as desired. For example, the present compositions may be in the form of a stable oil-in-water emulsion comprising a dispersed oily phase present at 1% to 50% (e.g., 1% to 30%) by volume, and a continuous aqueous phase present at 1% to 98% (e.g., 40% to 90%) by volume. When the present composition is in the form of an emulsion, the aqueous phase typically includes water, water miscible liquids, and/or water soluble materials, and the oily phase typically includes lipids, oils (e.g., silicone oils), oily materials, and/or materials that are not suitable for water or water soluble solvents.

The type of carrier utilized in the present composition depends on the type of product form desired for the composition. The topical composition useful in the subject invention may be made into a wide variety of product forms such as are known in the art. These include, but are not limited to, lotions, creams, gels, sticks, sprays, ointments, pastes, mousses and cosmetics (e.g., solid, semi-solid, or liquid make-up, including foundations, eye-makeup, pigmented or non-pigmented lip treatments, e.g., lipsticks, and the like). These product forms may comprise several types of carriers including, but not limited to, solutions, aerosols, emulsions, gels, solids, and liposomes. In some instances, the emulsions herein may include a gel network, such as described in G. M. Eccleston, Application of Emulsion Stability Theories to Mobile and Semisolid O/W Emulsions, Cosmetics & Toiletries, Vol. 101, November 1996, pp. 73-92.

Non-Volatile Dimethicone Fluid

The present composition includes between 5% and 30% (e.g., 10% to 30%, 10% to 25%, or even 12% to 20%) by weight of a non-volatile dimethicone fluid or blend of two or more non-volatile dimethicone fluids disposed in the oily phase of the composition, when the composition is in the form of an emulsion (e.g., oil-in-water, water-in-oil). As used herein, "dimethicone" means a polydimethylsiloxane compound having the formula:

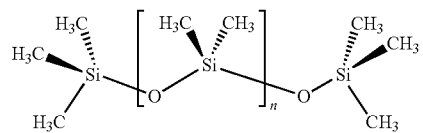

Non-volatile dimethicone fluids generally have a viscosity of greater than 5 cSt. The molecular weight of a dimethicone fluid depends on the length of the silicone polymer chains, which is also directly proportional to the viscosity of the silicone fluid. When two dimethicone fluids of different viscosities are blended together, the resulting blend will generally have a viscosity that falls somewhere between the viscosities of the individual fluids. The dimethicone fluids or blend of fluids herein exhibit a viscosity of between 1000 cSt and 10,000 Stokes (e.g., between 2000 cSt and 8,000 Stokes, 2500 cSt and 5000 Stokes, 3000 cSt and 1,000 Stokes, 3000 cSt and 50,000 cSt, 3,000 cSt and 15000 cSt, 3,000 cSt and 10,000 cSt, 1500 cSt and 10,000 cSt or even between 1500 cSt and 5,000 cSt). A suitable method of measuring viscosity is described in the Rheology Method below.

When two or more dimethicones are included in the composition, the dimethicones may be blended before, after, or while being added to the present composition. For example, it may be desirable to blend a 1000 cSt dimethicone with a 60,000 cSt dimethicone at a ratio of between 19:1 and 3:1, resulting in a blend that has a viscosity of between about 1500 cSt and about 3700 cSt. In another example, a 50 cSt dimethicone fluid may be blended with a 10,000 Stoke dimethicone fluid at a ratio of between 4:1 and 1:31 to obtain a blend with a viscosity of between 2500 cSt and 9,000 Stokes.

Silicone Elastomer

The present compositions include a silicone elastomer. Silicone elastomers are useful for reducing the tackiness of the composition and for providing a pleasant feel upon application. Thus, the silicone elastomer can be used to tailor the tackiness of the present compositions to a desired amount. The silicone elastomer may be in the form of spherical particles, non-spherical particles, or a gel.

One non-limiting example of a suitable class of non-spherical silicone elastomers is crosslinked organopolysiloxane (or siloxane) elastomer, which is generally described in U.S. Publication No. 2003/0049212. In this example, the non-spherical silicone elastomer may be present in the composition at about 0.1% to about 5% (e.g., 0.5% to about 2%, or even about 1%). The indicated percentages are understood to refer to the amount of dry elastomer, as opposed to the total amount of elastomer and solvent, used for example for storage and shipping.

Exemplary non-spherical crosslinked siloxane elastomers include the CTFA (Cosmetic, Toiletry, and Fragrance Association *International Cosmetic Ingredient Dictionary and Handbook,* 11th ed.) designated dimethicone/vinyl dimethicone crosspolymers supplied by a variety of suppliers including Dow Corning™, Momentive, Shin Etsu™ (KSG 15 and 16), and Grant Industries. Other exemplary nonemulsifying crosslinked siloxane elastomers include the CTFA designated dimethicone crosspolymers including Dow Corning™; e.g. DC 9040 and DC 9045 which are supplied as 12.5% elastomers in cyclodimethicone, and DC 9041 which is supplied as 16% elastomer in dimethicone).

In some instances, the present compositions may include spherical silicone elastomer particles. In addition to providing desirable feel properties to the composition, the spherical silicone elastomer particles can provide a light scattering effect that results in a smoother, more natural look to the skin. The spherical silicone elastomer particles may be present in the composition at 0.1% to 25% by weight of (e.g., from 0.5% to 20%, 1% to 15%, or even from 2% to 10%). The amount of spherical silicone elastomer powder in the composition is determined based on the particulate material being in neat form (i.e., not swollen in solvent). Some non-limiting examples of spherical silicone elastomer particles can be found in U.S. Publication No. 2015/0196464. Some particularly suitable examples of spherical silicone elastomer particles include: KSP-100, -101, -102, -103, -104, and -105, all from Shin Etsu; and DC9506 and DC 9701 from Dow Corning.

Water Swellable Material

The personal care composition herein may, optionally, include a water-swellable material that acts to bind the water in the composition. Water-swellable materials for use in the present composition may be natural or synthetic (e.g., water-swellable clay and superabsorbent polymers). The water-swellable material may be present at 0.01% to 5% by weight of the composition.

In some instances, the water-swellable material is a superabsorbent polymer ("SAP") present in the aqueous phase of the composition as a multitude of particles. When swollen, the SAP may provide a light, cool, and silky feel during application of the present composition. The SAP particles may have a dry, number-average particle size of 100 μm or less (e.g., 50 μm or less), for example, 2 μm to 100 μm, with a median particle size of 25, or even in the range of 2 μm to 40 μm with a median particle size of 12. The SAP particles may have a water-absorbing capacity ranging from 20 to 2000 times their own weight (i.e., 20 g to 2000 g of water absorbed per gram of absorbent polymer), for example, 30 to 1500 times, 50 to 1000 times, or even 400 times. The water-absorbing characteristics of the SAP particles herein are defined at standard temperature and pressure conditions for distilled water. For example, the value of the water-absorbing capacity of a SAP herein can be determined by dispersing 0.5 g of polymer(s) in 150 g of distilled water, waiting 20 minutes, filtering the non-absorbed solution through a suitable filter for 20 minutes, and weighing the non-absorbed water to determine how much was absorbed by the polymer. %). In some instances, the dynamic viscosity of an SAP solution in 1% distilled water is in the range of 20 to 30 Pa-s (e.g., 22 to 29 Pa-s) at pH 4 and in the range of 23 to 28 Pa-s at pH 7.

Once hydrated, the SAP particles suitable for use herein swell to form relatively soft beads that have a number average diameter of 10 μm to 150 μm (e.g., 20 μm to 130 μm, 30 μm-120 μm, 40 μm-100 μm, 50 μm-90 μm, or even about 70 μm). A suitable method of determining swollen particle size is described in co-pending U.S. Ser. No. 15/425,713 filed on Feb. 6, 2017 by Sunkel.

Some non-limiting examples of SAPs that may be suitable for use herein are crosslinked sodium polyacrylates such as those sold as: Octacare™ X100, X110, and RM100 by Avecia: Flocare™ GB300 and Flosorb 500 by SNF; Luquasorb™ 1003, 1010, 1100, and 1280 by BASF; Water Lock™ G400 and G430 (INCI name: Acrylamide/Sodium Acrylate Copolymer) by Grain Processing; Aqua Keep™ 10 SH NF, Aqua Keep 10 SH NFC, sodium acrylate crosspolymer-2, by Sumitomo Seika; starches grafted by an acrylic polymer (homopolymer or copolymer) and in particular by sodium polyacrylate (INCI name: Sodium Polyacrylate Starch), such as those sold as: Sanfresh™ ST-100C, ST100MC, and IM-300MC by Sanyo Chemical Industries; hydrolysed starches grafted by an acrylic polymer (homopolymer or copolymer), in particular the acryloacrylamide/sodium acrylate copolymer, (INCI name: Starch/Acrylamide/Sodium Acrylate Copolymer) such as those sold as: Water Lock™ A-240, A-180, B-204, D-223, A-100, C-200, and D-223 by Grain Processing. A particularly suitable example of an SAP is Makimousse™ 12 and Makimouse™ 25 supplied by Kobo Products, Inc.

The present composition may be made by conventional methods of making skin care compositions of the type described herein, which are known to those skilled in the art.

Other Optional Ingredients

The present composition may include a variety of optional ingredients that are known for use in personal care composition, as long as the optional ingredient(s) do not unduly alter product stability, aesthetics, or performance. The optional ingredients, when incorporated into the composition, should be suitable for contact with human keratinous tissue without undue toxicity, incompatibility, instability, allergic response, and the like within the scope of sound judgment. The CTFA *Cosmetic Ingredient Handbook*, Second Edition (1992) describes a wide variety of nonlimiting cosmetic and pharmaceutical ingredients. The compositions herein may from about 0.0001% to about 50%; from about 0.001% to about 20%; or, alternately, from about 0.01% to about 10%, by weight of the composition, of optional ingredients. Some non-limiting examples of optional ingredients include abrasives, absorbents, opacifying agents, colorings/colorants (e.g., pigments, dyes, and lakes), particles, essential oils, anti-caking agents, foaming agents, anti-foaming agents, oil control agents, binders, biological additives, vitamins, minerals, peptides, sugar amines, flavonoid compounds, anti-oxidants, preservatives, phytosterols, protease inhibitors, tyrosinase inhibitors, exfoliating agents, skin lightening agents, sunless tanning agents, thickeners, pH adjusters, anti-acne actives, anti-cellulite actives, anti-wrinkle actives, phytosterols and/or plant hormones, N-acyl amino acid compounds, antimicrobials, antifungals, moisturizers, emollients, humectants, lubricating agents, fragrances, anti-dandruff agents, buffering agents, bulking agents, chelating agents, biocides, denaturants, astringents, external analgesics, anti-inflammatory agents, sunscreen agents, film formers and/or polymers for aiding film-forming properties and substantivity of the composition, propellants, reducing agents, sequestrants, conditioning agents (see, e.g., U.S. Pat. Nos. 7,465,439, 7,041,767, and 7,217,777), and combinations of these. Some non-limiting examples of skin conditioning agents can be found in U.S. Pub. Nos. 2010/0272667 and 2008/0206373 and U.S. Pat. No. 8,790,720.

Method of Use

The personal care compositions herein are useful for regulating the condition of skin and/or hair while maintaining good stability. Regulating a condition of skin includes reducing the appearance of fine lines and/or wrinkles on the skin, reducing the appearance of eye bags and dark circles under the eyes, sagging skin, scars/marks, dimples, pores, stretch marks, roughness, skin surface blemishes, frown lines, expression lines, rhytides, blemishes, photodamage, crevices, and/or unevenness. Regulating the condition of skin also includes reducing the occurrence and/or appearance of acne.

The method of use may include identifying a target portion of keratinous tissue (e.g., a facial skin surface such as the forehead, perioral, chin, periorbital, nose, and/or cheek) in need of treatment and/or where treatment is desired and applying a safe and effective amount of the present composition to the target portion of tissue. The cosmetic active(s) may be incorporated into the present composition using conventional methods for combining active agents into cosmetic compositions. Without intending to be bound by theory, it is believed that application of an effective amount of the present composition to a target portion of keratinous tissue in need of treatment or where treatment is desired can provide the desired appearance benefit over the course of a treatment period.

The treatment period should be of sufficient time for the cosmetic active(s) in the present composition to provide the desired benefit to the target portion of keratinous tissue (e.g., improve appearance, increase moisturization). The treatment period may last for at least 1 week (e.g., about 2 weeks, 4 weeks, 8 weeks, or even 12 weeks). In some instances, the treatment period will extend over multiple months (i.e., 3-12 months) or multiple years. In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented portion of skin) while minimizing delivery to keratinous surfaces where treatment is not desired. In some instances, the composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces.

The present composition may be applied by a variety of means, including by rubbing, wiping or dabbing with hands or fingers, or by means of an implement and/or delivery enhancement device. Non-limiting examples of implements include a sponge or sponge-tipped applicator, a swab (for example, a cotton-tipped swab), a pen optionally comprising a foam or sponge applicator, a brush, a wipe, and combinations thereof. Non-limiting examples of delivery enhancement devices include magnetic, mechanical, electrical, ultrasonic and/or other energy devices. In some instances, the composition can be spread onto the skin to facilitate the separation of the aqueous phase from the oil-phase. When the aqueous and oil phases have separated, the composition may be left on the keratinous tissue. Alternatively, the composition may be allowed to remain on the skin for 5 seconds, 10 seconds, 30 seconds, or 1 minute prior to being rubbed into the keratinous tissue.

Methods

Tack Method

This method provides a suitable means for determining the tackiness of the compositions described herein. The method uses a texture analyzer to contact a probe with a film formed from the composition. The texture analyzer then measures the force needed to separate the probe from the composition film. Tack Force, Time Weighted Force Area, Mean Break Time, and the change in Break Time can all be determined by this method. The Tack Method is configured to run for a period of 100 minutes. It is believed, without being limited by theory, that the tackiness properties exhibited by a composition over the course of the Tack Test approximate the tackiness properties exhibited by the composition during the first few minutes (e.g., less than 10 minutes, between 30 seconds and 5 minutes, or between 1 minute and 3 minutes) of use of the composition by a user. It is also believed, without being limited by theory, that having a suitable tack force at the later time periods in the test (e.g., 60 minutes, 80 minutes, and/or 100 minutes), influences the moisturization perception of the user more than the tack force at earlier time periods in the test. Thus, time weighted force area is used to weight the tack force measurements toward the later time points, and thereby provide a more accurate prediction of the moisturization signal perceived by a user.

Figure 5:
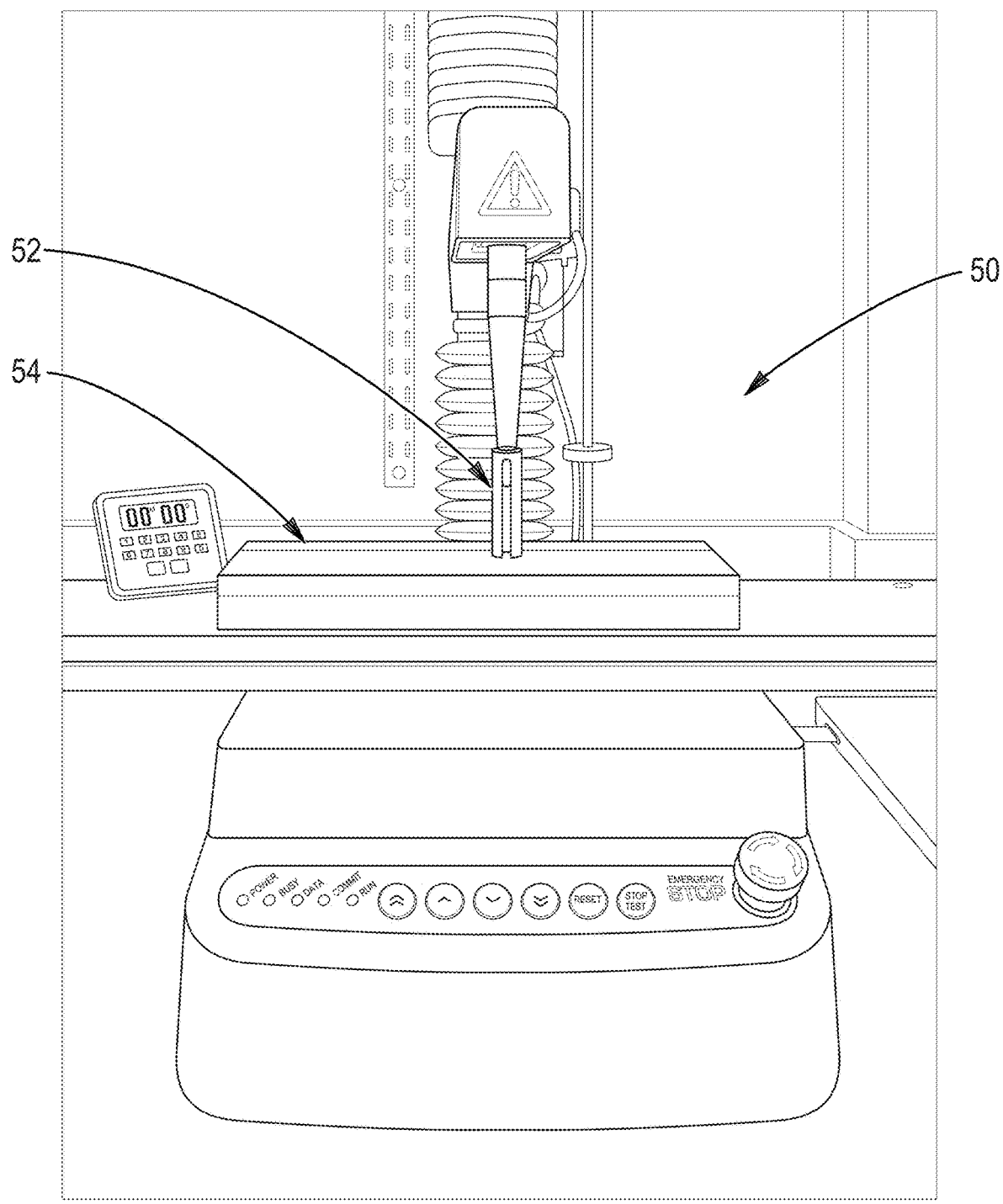
FIG. 5 illustrates a setup for the Tack Method.

FIG. 5 illustrates and exemplary test setup for the Tack Test. A TA.XT2i brand texture analyzer (available from Texture Technologies Corporation, MA) 50 or equivalent is used to measure the tack of a film formed from a composition of interest. The texture analyzer is equipped with a tack probe 52 in the form of a 12.75 mm diameter acrylic cylinder with a flat surface. During testing, the flat surface of the probe 52 is contacted with the surface of a film of the composition. Thus, the flat surface of the probe and the surface of the film must be parallel to one another during testing to ensure there is sufficient contact by the film across the effective test surface of the probe 52. The film is made by filling or overfilling (followed by draw down) a rectangular channel 54 (e.g., 25 cm long×30 mm wide a 0.25 mm deep) with the composition to be tested.

The test is conducted using an adhesive test protocol with a pretest speed of 0.10 mm/second, a test speed of 0.10 mm/sec and a post-test speed of 1.0 mm/sec. The applied force is 200 g, the return distance is 4 mm and the contact time is 5.0 sec. The trigger type to designate sample contact is set to automatic and the trigger force is 5.0 g. The test is run and at the following time increments immediately after the film is prepared: <1 minute (i.e., immediately following preparation of the film), 10, 20, 30, 40, 50, 60, 80, and 100 minutes. Each time point is run on a previously undisturbed/untested area of the sample. Each sample is run in triplicate and the averages are recorded.

Data extraction uses the portion of data that is collected as the probe pulls upward out of the sample. The tack force is the peak force of each test run. Time weighted force area is determined by the following formula:

$$\text{time weighted force area} = (t1 - t2) * \left[\frac{P1 - P2}{200}\right] * [(t1 + t2)/2]$$

Where:
t1=the later of the two times in the time range at which the measurement was taken;
t2=the earlier of the two times in the time range at which the measurement was taken;
P1=peak force in grams at time 1 in the pair of times being calculated; and
P2=peak force in grams at time 2 in the pair of times being calculated.
When calculating the difference between t1 and t2 or P1 and P2, the absolute value of the result is used to calculate time weighted force area.

Time Weighted Force Area is reported as the sum of the individual time weighted force area values calculated for each of the 8 time intervals (<1 min to 10 min, 10 min to 20 min, 20 min to 30 min, etc.).

Break time is determined by the width of the force curve. The start time of the Break time calculation is when the sign of the force exerted by the texture analyzer changes to positive from negative at time zero (i.e., the start of the test) and the time at which the force decays back to 0.0+/−0.02 from the peak force as the break time. Mean Break Time is reported as the average of the break times at 60, 80 and 100 minutes. The change in break time is the difference between the initial break time and the break time at 100 minutes.

Rheology Method

This method provides a suitable means of measuring the dynamic viscosity and yield point of the compositions herein. The instrument used in this method is a HAAKE RHEOSTRESS 600 brand rheometer, available from Thermo Fisher Scientific, MA, or equivalent. The instrument is set up to conduct a rotational ramp under controlled stress conditions, from 0.1 to 1000 Pa over 180 seconds, using a cone-and-plate geometry with a 35 mm diameter, 4 degree angle and a 0.140 mm gap. The temperature is set to 25° C. The instrument protocol is set up to collect 100 data points in a logarithmic distribution.

After conducting an automated plate-cone gap calibration, approximately 1.5 grams of a sample is placed on the center of the plate. The plate is positioned to provide a gap of 0.150 mm, and any excess material squeezed out of the perimeter gap of the cone is carefully trimmed away. The plate is then moved the final 0.1 mm to provide a 0.140 mm gap, and the measurement is initiated. At the end of the run, the data file is saved for subsequent plotting and analysis. The dynamic viscosity is reported as the value at or near 10 Pa of stress. Kinematic viscosity can by calculated by dividing the measured dynamic viscosity by the density of the sample at 25° C.

EXAMPLES

Example 1—Formulations

The formulas shown in Tables 1A and 1B provide non-limiting examples of the present composition. The Formulas shown in Table 2 are comparative examples of compositions that are not contemplated by the present invention. The compositions shown in Tables 1A, 1B, and 2 are oil-in-water emulsions prepared using conventional methods of making such compositions. The viscosity of the silicone blend in each composition was determined according to the Rheology Method, and the Mean Break Time and Time Weighted Force Area values were determined according to the Tack Method.

TABLE 1A

| Ingredient | N5 | N8 | N11 | N14 | N17 % | N20 | N23 | N26 | N29 |
|---|---|---|---|---|---|---|---|---|---|
| Water | qs | qs | qs | qs | qs | qs | qs | qs | qs |
| Polyacrylamide/C13-14 Isoparaffin-Laureth-7[1] | 2.0 | 2.0 | 2.0 | 2.0 | 2.0 | 2.0 | 2.0 | 2.0 | 2.0 |
| EDTA[2] | 0.05 | 0.05 | 0.05 | 0.05 | 0.05 | 0.05 | 0.05 | 0.05 | 0.05 |
| DMDM hydantoin (70%) and IPBC | 0.3 | 0.3 | 0.3 | 0.3 | 0.3 | 0.3 | 0.3 | 0.3 | 0.3 |
| Silicone fluid (2 cSt)[3] | 4.5 | 4.5 | 4.5 | 4.5 | 4.5 | 4.5 | 4.5 | 4.5 | 4.5 |
| Dimethicone crosspolymer in cyclopentasiloxane[4] | 5.0 | 5.0 | 5.0 | 5.0 | 5.0 | 5.0 | 5.0 | 5.0 | 5.0 |
| Dimethicone (50 cSt) | 12.8 | 9.37 | 7.39 | 3.75 | 0.5 | — | — | — | — |

TABLE 1A-continued

| Ingredient | N5 | N8 | N11 | N14 | N17 % | N20 | N23 | N26 | N29 |
|---|---|---|---|---|---|---|---|---|---|
| Dimethicone ($10^3$ cSt) | — | — | — | — | — | 15.2 | 14.4 | 12.8 | 7.5 |
| Dimethicone ($6 \times 10^4$ cSt) | — | — | — | — | — | 0.8 | 1.6 | 3.2 | 2.5 |
| Dimethicone ($10^6$ cSt) | 3.2 | 6.63 | 8.61 | 12.25 | 15.5 | — | — | — | — |
| Polysorbate 20 | 0.05 | 0.05 | 0.05 | 0.05 | 0.05 | 0.05 | 0.05 | 0.05 | 0.05 |
| Polyoxyethylene(4) lauryl ether[5] | 0.05 | 0.05 | 0.05 | 0.05 | 0.05 | 0.05 | 0.05 | 0.05 | 0.05 |
| Viscosity of dimethicone blend (cSt) | 2,790 | 31,810 | 102,900 | 425,000 | 873,400 | 1,495 | 2,040 | 3,469 | 3,278 |
| Mean Break Time (sec) | 0.328 | 0.503 | 0.638 | 0.653 | 0.562 | 0.342 | 0.326 | 0.401 | 0.307 |
| Time Weighted Force Area | 50,014 | 68,946 | 86,513 | 117,544 | 105,738 | 60,921 | 56,833 | 70,823 | 68,256 |

[1] SEPIGEL 305 available from Seppic.
[2] Ethylenediaminetetraacetic acid
[3] XIAMETER from Dow Corning
[4] DC9045 from Dow Corning
[5] BRIJ 30 from Sigma-Aldrich

TABLE 1B

| Ingredient | N30 | N31 | N33 | N34 | N36 % | N38 | N39 | N40 | N41 |
|---|---|---|---|---|---|---|---|---|---|
| Water | qs | qs | qs | qs | qs | qs | qs | qs | qs |
| Polyacrylamide/C13-14 Isoparaffin-Laureth-7 | 2.0 | 2.0 | 2.0 | 2.0 | 2.0 | 2.0 | 2.0 | 2.0 | 2.0 |
| EDTA | 0.05 | 0.05 | 0.05 | 0.05 | 0.05 | 0.05 | 0.05 | 0.05 | 0.05 |
| DMDM hydantoin (70%) and IPBC | 0.3 | 0.3 | 0.3 | 0.3 | 0.3 | 0.3 | 0.3 | 0.3 | 0.3 |
| Silicone fluid (2 cSt) | 4.5 | 4.5 | 4.5 | 4.5 | 4.5 | 4.5 | 4.5 | 4.5 | 4.5 |
| Dimethicone crosspolymer in cyclopentasiloxane | 5.0 | 5.0 | 5.0 | 5.0 | 5.0 | 10.0 | 15.0 | 20.0 | 5.0 |
| Dimethicone (50 cSt) | — | — | — | — | — | — | — | — | — |
| Dimethicone ($10^3$ cSt) | 12.0 | 15.0 | 9.6 | 12.0 | 8.0 | 15.0 | 15.0 | 15.0 | 10.8 |
| Dimethicone ($6 \times 10^4$ cSt) | 4.0 | 5.0 | 6.4 | 8.0 | 8.0 | 5.0 | 5.0 | 5.0 | 7.2 |
| Dimethicone ($10^6$ cSt) | — | — | — | — | — | — | — | — | — |
| Polysorbate 20 | 0.05 | 0.05 | 0.05 | 0.05 | 0.05 | 0.05 | 0.05 | 0.05 | 0.05 |
| Polyoxyethylene(4) lauryl ether | 0.05 | 0.05 | 0.05 | 0.05 | 0.05 | 0.05 | 0.05 | 0.05 | 0.05 |
| Viscosity of dimethicone blend (cSt) | 3,728 | 3,728 | 8,750 | 8,750 | 14,010 | 3,728 | 3,728 | 3,728 | 8,750 |
| Mean Break Time (sec) | 0.476 | 0.401 | 0.491 | 0.671 | 0.557 | 0.434 | 0.432 | 0.484 | 0.594 |
| Time Weighted Force Area | 74,675 | 82,879 | 77,343 | 104,020 | 83,811 | 63,346 | 65,061 | 67,678 | 95,733 |

TABLE 2

| Ingredient | N2 % | N28 |
|---|---|---|
| Water | qs | qs |
| Polyacrylamide/C13-14 Isoparaffin-Laureth-7 | 2.0 | 2.0 |
| EDTA | 0.05 | 0.05 |
| DMDM hydantoin (70%) and IPBC | 0.3 | 0.3 |
| Silicone fluid (2 cSt) | 4.5 | 4.5 |
| Dimethicone crosspolymer in cyclopentasiloxane | 5.0 | 5.0 |
| Dimethicone (50 cSt) | 14.4 | — |
| Dimethicone ($10^3$ cSt) | — | 3.75 |
| Dimethicone ($6 \times 10^4$ cSt) | — | 1.25 |

TABLE 2-continued

| Ingredient | N2 % | N28 |
|---|---|---|
| Dimethicone ($10^6$ cSt) | 1.6 | — |
| Polysorbate 20 | 0.05 | 0.05 |
| Polyoxyethylene(4) lauryl ether | 0.05 | 0.05 |
| Viscosity of dimethicone blend (cSt) | 478 | 3,728 |
| Mean Break Time (sec) | 0.270 | 0.203 |
| Time weighted Force Area | 43,770 | 31,389 |

Example 2—Tack Force and Break Time

Figure 3:
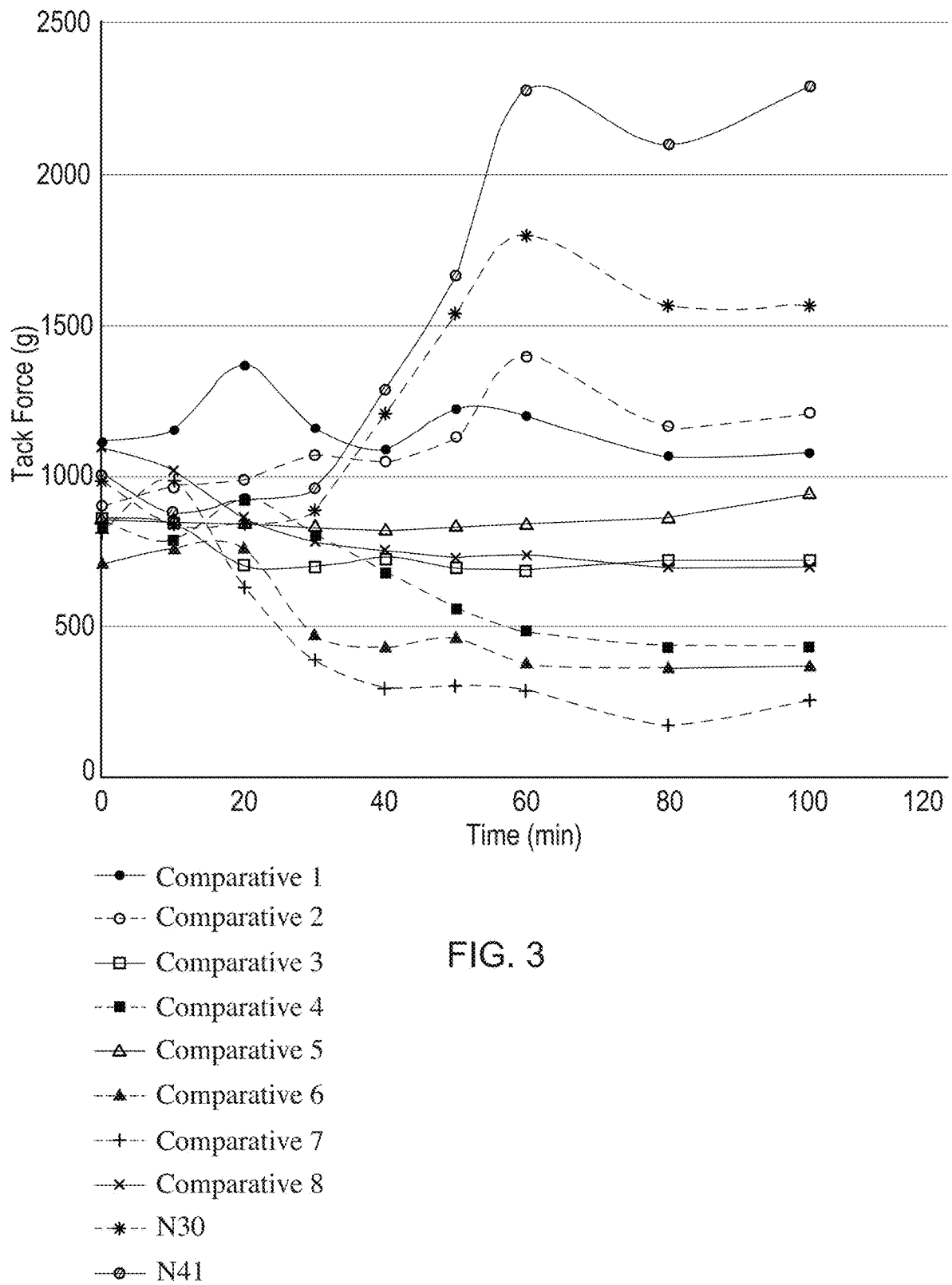
FIG. 3 is a plot of tack force versus time.
Figure 4:
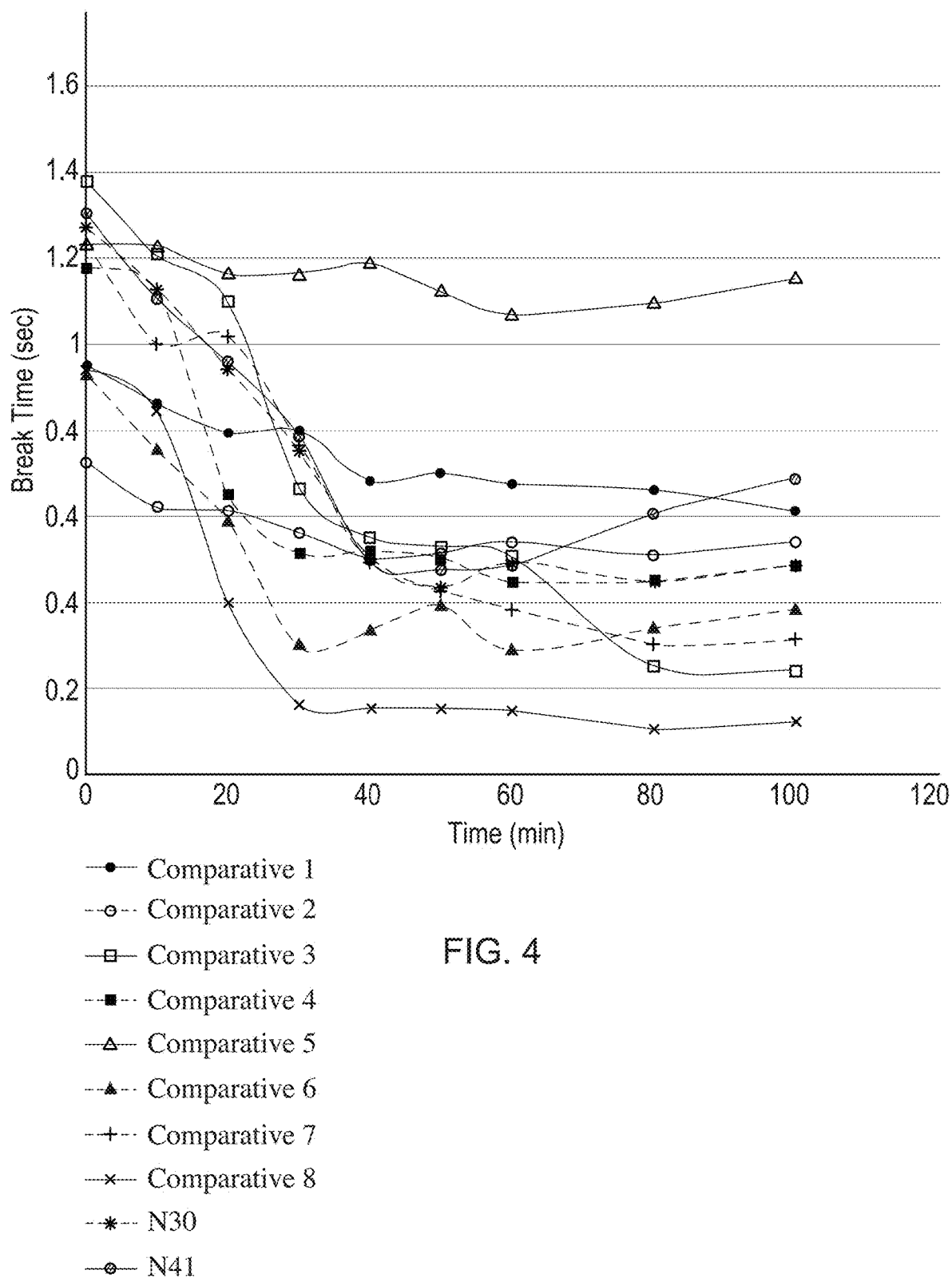
FIG. 4 is a plot of break time versus time.

This example compares the tack force of the compositions in Tables 1A, 1B and 2 to eight conventional skin care products marketed as providing a skin moisturizing benefit. The tack force values and break time values were generated according to the Tack Method. Tack force values are shown in Table 3. The tack force values for N30, N41, and the conventional skin care products are illustrated in FIG. 3. Break Time values are shown in Table 4, and the Break Time values for N30, N41 and the conventional skin care products are illustrated in FIG. 4. As can be seen in FIG. 3 and FIG. 4, the present compositions provide a desirable tack forces and break times at the appropriate times.

TABLE 3

| | Tack Force (g) | | | | | | | | |
|---|---|---|---|---|---|---|---|---|---|
| Composition | Initial | 10 min | 20 min | 30 min | 40 min | 50 min | 60 min | 80 min | 100 min |
| N2 | 991 | 772 | 734 | 878 | 1154 | 1003 | 896 | 815 | 805 |
| N5 | 941 | 782 | 755 | 841 | 1225 | 1224 | 1079 | 918 | 971 |
| N8 | 956 | 798 | 784 | 910 | 1106 | 1528 | 1557 | 1323 | 1689 |
| N11 | 940 | 761 | 827 | 789 | 1190 | 1669 | 1759 | 1825 | 2449 |
| N14 | 829 | 762 | 806 | 897 | 1999 | 2600 | 2686 | 2681 | 2465 |
| N17 | 787 | 698 | 875 | 2120 | 2267 | 2624 | 2275 | 2165 | 1969 |
| N20 | 997 | 935 | 937 | 927 | 1437 | 1439 | 1333 | 1191 | 1120 |
| N23 | 988 | 950 | 849 | 893 | 1729 | 1496 | 1114 | 1078 | 972 |
| N26 | 1066 | 936 | 939 | 942 | 1035 | 1442 | 1708 | 1540 | 1364 |
| N28 | 1196 | 925 | 851 | 792 | 751 | 851 | 745 | 391 | 590 |
| N29 | 1090 | 900 | 838 | 831 | 1238 | 1500 | 1416 | 1345 | 1127 |
| N30 | 985 | 841 | 843 | 887 | 1210 | 1541 | 1796 | 1568 | 1566 |
| N31 | 947 | 958 | 1119 | 1820 | 1855 | 1810 | 1734 | 1677 | 1530 |
| N33 | 1008 | 805 | 800 | 856 | 983 | 1243 | 1629 | 1818 | 1889 |
| N34 | 923 | 874 | 924 | 964 | 1253 | 1673 | 2076 | 2659 | 2447 |
| N36 | 769 | 820 | 787 | 1469 | 1593 | 1709 | 1676 | 1905 | 1675 |
| N38 | 902 | 849 | 774 | 807 | 1417 | 1623 | 1428 | 1235 | 1204 |
| N39 | 875 | 791 | 813 | 1438 | 1340 | 1373 | 1319 | 1413 | 1158 |
| N40 | 832 | 788 | 728 | 1153 | 1606 | 1438 | 1391 | 1433 | 1296 |
| N41 | 1003 | 879 | 922 | 962 | 1286 | 1663 | 2279 | 2099 | 2290 |
| Comparative[1] | 1114 | 1152 | 1366 | 1160 | 1088 | 1224 | 1203 | 1064 | 1078 |
| Comparative[2] | 900 | 966 | 988 | 1070 | 1047 | 1130 | 1395 | 1167 | 1209 |
| Comparative[3] | 842 | 787 | 923 | 807 | 683 | 562 | 487 | 440 | 439 |
| Comparative[4] | 818 | 812 | 828 | 909 | 902 | 967 | 952 | 961 | 898 |
| Comparative[5] | 852 | 848 | 841 | 829 | 818 | 832 | 841 | 862 | 942 |
| Comparative[6] | 708 | 762 | 759 | 474 | 436 | 463 | 377 | 364 | 372 |
| Comparative[7] | 814 | 984 | 635 | 391 | 299 | 305 | 290 | 174 | 261 |
| Comparative[8] | 1097 | 1020 | 863 | 785 | 755 | 732 | 739 | 701 | 703 |

[1]MOISTURE SURGE INTENSE brand Skin Hydrator from Clinique, NY.
[2]REVITALIZING SUPREME brand global anti-aging cream from Estee Lauder, NY.
[3]RESILIENCE LIFT NIGHT brand face and neck cream from Estee Lauder, NY.
[4]REVITALIZING SUPREME brand skin cream from Estee Lauder, NY.
[5]REVITALIFT TRIPLE POWER brand lotion moisturizer from L'Oreal, France.
[6]WHITE PERFECT brand watery day cream from L'Oreal, France.
[7]TRIPLE AGE REPAIR brand night moisturizer from Neutrogena, CA.
[8]RAPID WRINKLE REPAIR brand moisturizer from Neutrogena, CA.

TABLE 4

| | Break Time (seconds) | | | | | | | | |
|---|---|---|---|---|---|---|---|---|---|
| Composition | Initial | 10 min | 20 min | 30 min | 40 min | 50 min | 60 min | 80 min | 100 min |
| N2 | 1.19 | 0.94 | 0.64 | 0.50 | 0.35 | 0.35 | 0.31 | 0.26 | 0.23 |
| N5 | 1.21 | 0.84 | 0.77 | 0.48 | 0.33 | 0.38 | 0.33 | 0.32 | 0.34 |
| N8 | 1.23 | 1.20 | 0.85 | 0.47 | 0.41 | 0.43 | 0.48 | 0.49 | 0.54 |
| N11 | 1.10 | 1.18 | 0.91 | 0.50 | 0.41 | 0.57 | 0.59 | 0.57 | 0.76 |
| N14 | 1.40 | 1.15 | 0.82 | 0.47 | 0.57 | 0.68 | 0.67 | 0.70 | 0.60 |
| N17 | 1.36 | 0.75 | 0.38 | 0.50 | 0.59 | 0.67 | 0.57 | 0.59 | 0.53 |
| N20 | 1.26 | 1.02 | 0.81 | 0.64 | 0.43 | 0.40 | 0.36 | 0.33 | 0.34 |
| N23 | 1.22 | 1.01 | 0.86 | 0.66 | 0.49 | 0.38 | 0.38 | 0.32 | 0.28 |
| N26 | 1.24 | 1.02 | 0.91 | 0.68 | 0.52 | 0.38 | 0.46 | 0.41 | 0.33 |
| N28 | 1.28 | 1.13 | 0.89 | 0.60 | 0.42 | 0.25 | 0.21 | 0.20 | 0.20 |
| N29 | 1.33 | 1.10 | 0.87 | 0.69 | 0.41 | 0.36 | 0.34 | 0.29 | 0.29 |
| N30 | 1.27 | 1.13 | 0.95 | 0.76 | 0.51 | 0.44 | 0.49 | 0.45 | 0.49 |

TABLE 4-continued

| Composition | Break Time (seconds) | | | | | | | | |
|---|---|---|---|---|---|---|---|---|---|
| | Initial | 10 min | 20 min | 30 min | 40 min | 50 min | 60 min | 80 min | 100 min |
| N31 | 0.87 | 0.64 | 0.34 | 0.45 | 0.56 | 0.46 | 0.42 | 0.42 | 0.36 |
| N33 | 1.61 | 1.34 | 1.07 | 1.01 | 0.71 | 0.47 | 0.48 | 0.50 | 0.50 |
| N34 | 1.34 | 1.14 | 1.04 | 0.88 | 0.62 | 0.51 | 0.56 | 0.69 | 0.76 |
| N36 | 1.09 | 0.81 | 0.50 | 0.34 | 0.43 | 0.50 | 0.45 | 0.47 | 0.75 |
| N38 | 1.50 | 1.20 | 0.95 | 0.78 | 0.46 | 0.47 | 0.56 | 0.40 | 0.34 |
| N39 | 1.37 | 1.06 | 0.82 | 0.51 | 0.55 | 0.47 | 0.46 | 0.42 | 0.42 |
| N40 | 1.39 | 1.05 | 0.88 | 0.48 | 0.55 | 0.54 | 0.51 | 0.45 | 0.49 |
| N41 | 1.3 | 1.11 | 0.96 | 0.79 | 0.5 | 0.48 | 0.49 | 0.61 | 0.69 |
| Comparative[1] | 0.95 | 0.86 | 0.79 | 0.80 | 0.68 | 0.70 | 0.68 | 0.66 | 0.61 |
| Comparative[2] | 0.73 | 0.62 | 0.61 | 0.56 | 0.50 | 0.52 | 0.54 | 0.51 | 0.54 |
| Comparative[3] | 1.38 | 1.21 | 1.41 | 0.67 | 0.55 | 0.76 | 0.51 | 0.25 | 0.24 |
| Comparative[4] | 0.8 | 0.66 | 0.66 | 0.64 | 0.56 | 0.57 | 0.54 | 0.55 | 0.61 |
| Comparative[5] | 1.23 | 1.23 | 1.17 | 1.16 | 1.19 | 1.12 | 1.07 | 1.10 | 1.15 |
| Comparative[6] | 0.94 | 0.76 | 0.59 | 0.30 | 0.34 | 0.40 | 0.29 | 0.34 | 0.39 |
| Comparative[7] | 0.94 | 0.85 | 0.40 | 0.16 | 0.16 | 0.16 | 0.15 | 0.11 | 0.13 |
| Comparative[8] | 1.24 | 1.00 | 1.02 | 0.77 | 0.50 | 0.43 | 0.39 | 0.31 | 0.32 |

Examples/Combinations

A. A personal care composition that exhibits an improved moisturization signal, comprising:
1) about 5% to 30%, preferably about 10%-30%, by weight of the composition, of a blend of at least two dimethicone fluids, wherein the blend of dimethicone fluids exhibits a viscosity of greater than about 1000 centistokes (cSt) according to the Rheology Method; and
2) a dermatologically acceptable carrier,
wherein the composition exhibits a Time Weighted Force Area of between about $5 \times 10^4$ and about $12 \times 10^4$ and a Mean Break Time of between about 0.30 and about 0.75

B. The personal care composition of paragraph A, wherein the blend of dimethicone fluids has a viscosity of less than about 10,000 Stokes.

C. The personal care composition of paragraph A or B, wherein a first dimethicone fluid in the blend has a viscosity of about 1000 cSt and a second dimethicone in the blend has a viscosity of about 60,000 cSt.

D. The personal care composition of paragraph C, wherein the first and second dimethicone fluids are present at a ratio of between about 20:1 and about 1:1.

E. The personal care composition of any preceding paragraph, further comprising about 1% to about 30%, by weight, of a silicone elastomer.

F. The personal care composition of paragraph E, further comprising a weight ratio of silicone elastomer to dimethicone fluid of about 1:10 to about 1:1.

G. The personal care composition of any preceding paragraph, further comprising an initial break time of greater than about 1.0.

H. The personal care composition of any preceding paragraph, further comprising a tack force at 60 minutes, 80 minutes, or 100 minutes of greater than about 1000.

I. The personal care composition of any preceding paragraph, further comprising a silicone-in-water emulsion.

J. The personal care composition of any preceding paragraph, further comprising about 0.01% to 5%, by weight, of a superabsorbent polymer.

K. The personal care composition of paragraph J, further comprising an aqueous phase, wherein the superabsorbent polymer is present in the aqueous phase.

L. The personal care composition of paragraph J or K, wherein the superabsorbent polymer has a non-swollen, number average particle size of between about 2 microns and about 100 microns.

M. The personal care composition of any preceding paragraph, further comprising a skin care active selected from vitamins, minerals, peptides, oil control agents, antioxidants, anti-inflammatory agents, moisturizing agents, emollients, humectants, exfoliating agents, skin lightening agents, sunscreens, anti-acne actives, anti-wrinkle actives, antimicrobials, and combinations of these.

N. The personal care composition of paragraph M, wherein the skin care active is a vitamin comprising a stabilized retinoid.

O. The personal care composition of paragraph N, wherein the retinoid is stabilized by a fatty acid ester present at a ratio of fatty acid ester to retinoid of 5:1 to 50:1.

P. The personal care composition of paragraph O, wherein the fatty acid ester comprises capric/caprylic triglyceride.

Q. A method of cosmetically treating a skin condition with a composition that provides an improved moisturization signal, comprising:
1) identifying a target portion of skin where skin moisturization is needed or desired; and
2) applying the skin care composition of any preceding paragraph to the target portion of skin.

R. A personal care composition, comprising:
1) about 10% to about 20%, by weight, of a dimethicone fluid, wherein the dimethicone fluids has a viscosity of between about 1000 cSt and about 1,000,000 cSt according to the Rheology Method, and a Time Weighted Force Area of between about $5 \times 10^4$ and about $12 \times 10^4$ and a mean break time of between about 0.30 and 0.75 according to the Tack Method; and
2) a dermatologically acceptable carrier.

S. The personal care composition of paragraph R, further comprising an initial break time of greater than about 1.0.

T. The personal care composition of paragraph R or S, further comprising a tack force of greater than about 1000 at 60 minutes, 80 minutes, and/or 100 minutes.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care composition, comprising:
    a) about 5% to about 30%, by weight of the composition, of a blend of at least two dimethicone fluids, wherein the blend of dimethicone fluids exhibits a viscosity of greater than about 1000 centistokes (cSt) according to the Rheology Method; and
    b) a dermatologically acceptable carrier,
    wherein the composition exhibits a Time Weighted Force Area of between about $5 \times 10^4$ grams-minute$^2$ and about $12 \times 10^4$ grams-minute$^2$—and a Mean Break Time of between about 0.30 seconds and about 0.75 seconds according to the Tack Method, and wherein the skin care composition is in the form of a cream or lotion.

2. The personal care composition of claim 1, wherein the blend of dimethicone fluids has a viscosity of less than about 10,000 Stokes.

3. The personal care composition of claim 1, wherein a first dimethicone fluid in the blend has a viscosity of about 1000 cSt and a second dimethicone in the blend has a viscosity of about 60,000 cSt.

4. The personal care composition of claim 3, wherein the first and second dimethicone fluids are present at a ratio of between about 20:1 and about 1:1.

5. The personal care composition of claim 1, further comprising about 1% to about 30%, by weight, of a silicone elastomer.

6. The personal care composition of claim 5, further comprising a weight ratio of silicone elastomer to dimethicone fluid of about 1:10 to about 1:1.

7. The personal care composition of claim 1, further comprising an initial break time of greater than about 1.0 second.

8. The personal care composition of claim 1, further comprising a tack force at 60 minutes, 80 minutes, or 100 minutes of greater than about 1000 grams.

9. The personal care composition of claim 1, further comprising about 0.01% to about 5%, by weight, of a superabsorbent polymer.

10. The personal care composition of claim 1, further comprising an aqueous phase, wherein the superabsorbent polymer is present in the aqueous phase.

11. The personal care composition of claim 10, wherein the superabsorbent polymer has a non-swollen, number average particle size of between about 2 microns and 100 microns.

12. The personal care composition of claim 1, further comprising a skin care active selected from the group consisting of vitamins, minerals, peptides, oil control agents, anti-oxidants, anti-inflammatory agents, moisturizing agents, emollients, humectants, exfoliating agents, skin lightening agents, sunscreens, anti-acne actives, anti-wrinkle actives, antimicrobials, and combinations of these.

13. The personal care composition of claim 12, wherein the skin care active is a vitamin comprising a stabilized retinoid.

14. The personal care composition of claim 13, wherein the retinoid is stabilized by a fatty acid ester present at a ratio of fatty acid ester to retinoid of about 5:1 to about 50:1.

15. The personal care composition of claim 11, wherein the fatty acid ester comprises capric/caprylic triglyceride.

16. A method of cosmetically treating a skin condition with a composition that provides an improved moisture perception, comprising:
    a) identifying a target portion of skin where skin moisturization is needed or desired; and
    b) applying the skin care composition of claim 1 to the target portion of skin.

* * * * *